(12) United States Patent
Bordier et al.

(10) Patent No.: US 6,641,802 B2
(45) Date of Patent: Nov. 4, 2003

(54) AMINO ACID COMPOUNDS AND PHOTOPROTECTING COMPOSITIONS COMPRISED THEREOF

(75) Inventors: Thierry Bordier, Tremblay (FR); Michel Philippe, Wissous (FR)

(73) Assignee: Societe L'Oreal S.A., Paris (FR)

( * ) Notice: Subject to any disclaimer, the term of this patent is extended or adjusted under 35 U.S.C. 154(b) by 11 days.

(21) Appl. No.: 10/026,607

(22) Filed: Dec. 27, 2001

(65) Prior Publication Data
US 2002/0150545 A1 Oct. 17, 2002

Related U.S. Application Data

(63) Continuation of application No. PCT/FR01/01137, filed on Apr. 12, 2001.

(30) Foreign Application Priority Data

Apr. 27, 2000 (FR) .............................. 00 05393

(51) Int. Cl.$^7$ ............................ A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| 4,367,390 A | * | 1/1983 | Balleys et al. |
| 5,166,355 A | * | 11/1992 | Leistner et al. |
| 5,237,071 A | * | 8/1993 | Leistner et al. |

* cited by examiner

Primary Examiner—Shelley A. Dodson
(74) Attorney, Agent, or Firm—Burns, Doane, Swecker & Mathis, L.L.P.

(57) ABSTRACT

Amino acid compounds having the formula (I):

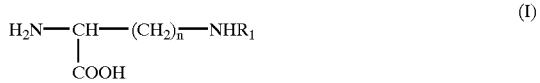

are well suited for the UV-photoprotection of human skin and/or hair, as well as for the UV-photoprotection of a wide variety of photosensitive industrial materials/substrates, e.g., plastics, glasses, textiles, etc.

16 Claims, No Drawings

AMINO ACID COMPOUNDS AND PHOTOPROTECTING COMPOSITIONS COMPRISED THEREOF

CROSS-REFERENCE TO PRIORITY/PCT APPLICATIONS

This application claims priority under 35 U.S.C. §119 of FR-00/05393, filed Apr. 27, 2000, and is a continuation of PCT/FR01/01137, filed Apr. 12, 2001 and designating the United States (published in the French language on Nov. 1, 2001 as WO 01/81297 A1; the title and abstract were also published in English), both hereby expressly incorporated by reference.

BACKGROUND OF THE INVENTION

1. Technical Field of the Invention

The present invention relates to novel amino acid compounds, to a process for the preparation thereof and to their use as photoprotecting UV screening agents, in particular when formulated as cosmetic compositions.

The present invention also relates to a regime/regimen employing the aforesaid novel compounds for the protection of the skin and/or hair against the deleterious effects of ultraviolet radiation and for the photoprotection of any other material or substrate which is sensitive to UV radiation (inorganic or organic glasses, plastics, foodstuffs, paints, etc.).

2. Description of the Prior Art

It is known to this art that light radiation of wavelengths of from 280 nm to 400 nm enables human skin to brown and that radiation of wavelengths of from 280 nm to 320 nm, known as UV-B radiation, causes erythemas and skin burns which can harm the development of natural tanning. For these reasons and also for aesthetic reasons, there exists a continual demand for means for controlling this natural tanning, for the purpose of thus controlling the color of the skin; it is thus advisable to screen out this UV-B radiation.

It is also known to this art that UV-A radiation, of wavelengths of from 320 nm to 400 nm, which causes the skin to brown, is apt to also effect a detrimental change therein, especially in the case of sensitive skin or skin which is continually exposed to solar radiation. In particular, UV-A radiation causes a loss of skin elasticity and the appearance of wrinkles, resulting in premature aging. It promotes the triggering of the erythemal reaction or accentuates this reaction in certain individuals and can even be the cause of phototoxic or photoallergic reactions. Thus, for aesthetic and cosmetic reasons, such as preservation of the natural elasticity of the skin, for example, more and more individuals wish to control the effect of UV-A radiation on their skin. It is thus desirable to screen out the UV-A radiation as well.

Thus, for the purpose of providing protection of the skin and hair against all UV radiation which is as complete and as efficient as possible, sunscreen compositions are typically applied/administered that contain combinations of screening agents active in the UV-A region and screening agents active in the UV-B region.

Benzylidenecamphorsulfonamide compounds derived from amino acids are known to the prior art and, in particular, are described in U.S. Pat. No. 5,004,594 as UV screening agents, especially in the cosmetic field. Other sunscreens derived from amino acids, namely, amide compounds of para-methoxycinnamic acid and of urocanic acid, have also been described, in FR-2,579,461. These amino acid derivatives are capable of absorbing in the UV-B region and/or the UV-A region. They are soluble in those solvents conventionally employed in anti-sun/sunscreen formulations and, in particular, in oils. These exhibit no activity with regard to the scattering of light.

SUMMARY OF THE INVENTION

In the field of photoprotection, it has now surprisingly and unexpectedly been determined that certain amino acid compounds, insoluble or substantially insoluble in water and the conventional organic solvents, are capable both of absorbing and of scattering UV radiation in anti-sun/sunscreen formulations. Thus, the subject novel amino acid compounds in accordance with the invention provide a stronger photoprotection in comparison with the known amino acid derivatives.

The present invention thus features compositions well suited for photoprotecting a material/substrate sensitive to ultraviolet radiation, in particular to solar radiation, comprising an effective amount of at least one compound having the structural formula (I):

$$H_2N-\underset{\underset{COOH}{|}}{CH}-(CH_2)_{\overline{n}}-NHR_1 \quad (I)$$

in which n is an integer ranging from 1 to 4; and $R_1$ is one of the following radicals of formula (1), (2), (3), (4), (5), (6) or (7):

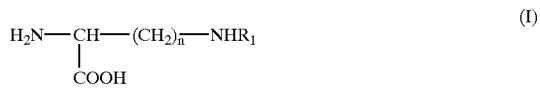

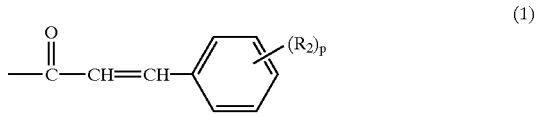

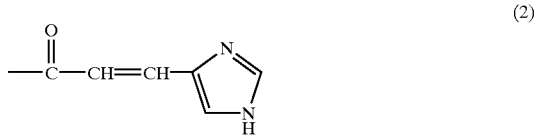

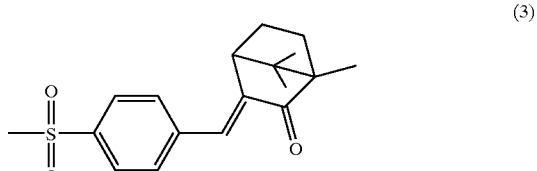

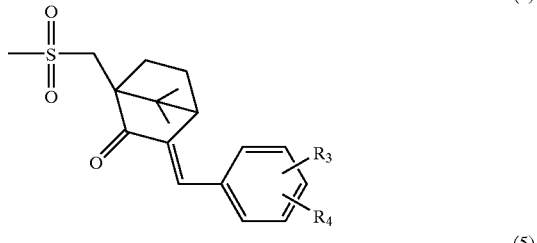

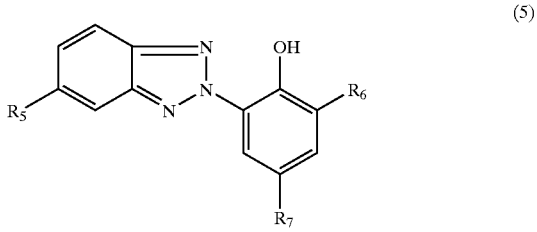

(6)

(7)

in which p is an integer ranging from 1 to 3; $R_2$ is hydrogen, a $C_1$–$C_8$ alkyl radical, a $C_1$–$C_8$ O-alkyl radical, or a $C_1$–$C_8$ O-acyl radical; $R_3$ and $R_4$, which may be identical or different, are each H or halogen or $C_1$–$C_8$ alkyl or alkoxy or a radical of the following formula (8):

(8)

$R_5$ is a hydrogen or halogen atom, a $C_1$–$C_8$ alkyl or alkoxy radical, or a divalent radical:

$R_6$ is a hydrogen atom, a $C_1$–$C_8$ alkyl radical or a divalent radical:

with the proviso that at least one of the two substituents $R_5$ and $R_6$ is the divalent radical:

$R_7$ is a $C_1$–$C_8$ alkyl radical; and the acid or base salts thereof.

DETAILED DESCRIPTION OF BEST MODE AND SPECIFIC/PREFERRED EMBODIMENTS OF THE INVENTION

More particularly according to the present invention, when the sensitive material/substrate to be protected is human skin and/or hair, the subject compositions are provided in the form of cosmetic compositions comprising, formulated into a topically applicable, cosmetically acceptable vehicle, diluent or carrier therefor, an effective photoprotecting amount of at least one compound of formula (I).

The compounds of formula (I) in accordance with the invention can be provided in the form of a mixture of isomers or of a pure isomer (regio-, enantio- or geometric isomerism).

Exemplary preferred compounds of formula (I) are ornithine (n=3) derivatives and lysine (n=4) derivatives.

More particularly exemplary compounds of formula (I) in accordance with the invention are:

$N^\epsilon$-cinnamoyl-L-lysine;

$N^\epsilon$-(4-methoxycinnamoyl)-L-lysine;

$N^\epsilon$-[4-(4,7,7-trimethyl-3-oxobicyclo[2.2.1]hept-2ylidenemethyl) benzenesulfonyl]-L-lysine.

$N^\epsilon$-Cinnamoyl-L-lysine is described in the article "Syntheses of photosensitive poly(amino acids)", Nasawa M. and Kamogawa H., *Bulletin of the Chemical Society of Japan*, Vol. 48 (9), pages 2588–2591 (1975). 3-[(1-Oxo-3-phenyl-2-propenyl)amino]-L-alanine and its monohydrochloride have been described in the article "Structural determinants of inhibitory activity of $N^3$(4-methoxyfumaroyl)-L-2,3-diaminopropanoic acid towards glucosamine-6-phosphate synthase", Andruszkiewicz R., *Polish J. Chem.*, 67, pages 673–683 (1993).

Accordingly, this invention also features the novel amino acid compounds corresponding to the formula (I) as defined above, with the exception of $N^\epsilon$-cinnamoyl-L-lysine and of 3-[(1-oxo-3-phenyl-2propenyl)amino]-L-alanine and its monohydrochloride.

Too, the present invention features a process for the preparation of the novel compounds of formula (I) described above, comprising:

(a) in a first stage, complexing the $NH_2$—CH(COOH)— moiety of an amino acid monohydrochloride having the following formula (II):

$$H_2N-CH(COOH)-(CH_2)_n-NH_2 \cdot HCl \quad (II)$$

with a copper sulfate in a basic medium (for example, an aqueous sodium hydroxide solution) in the presence of a polar organic solvent (such as tetrahydrofuran, dimethylformamide or acetone);

(b) in a second stage, reacting, in the presence of a polar organic solvent, the copper complex thus obtained with an acid chloride $R_1COCl$ or a sulfonyl chloride $R_1SO_2Cl$, wherein $R_1$ is as defined above in the formula (I);

(c) in a third stage, recovering, by filtration, the precipitate obtained in stage (b); and (d) decomplexing the product thus obtained with a sequestering agent (for example, ethylenediaminetetraacetic acid).

These amino acid derivatives are insoluble or substantially insoluble in water and in the conventional organic solvents usual in the cosmetics field, in particular oils.

By the term "insoluble or substantially insoluble compounds" are intended compounds having a solubility in water of less than 2% by weight, with a solubility in liquid petrolatum of less than 3% by weight and, finally, with a solubility in a mixture of triglyceride esters, such as "Miglyol 812", marketed by Dynamit Nobel, of less than 5%, also by weight.

The amino acid compounds in accordance with the present invention can be reduced to a suitable particulate form by any ad hoc means, such as, in particular, dry milling or milling in a solvent medium, sieving, atomization, micronization or spraying. The mean size of the particles will generally be less than 50 µm and more preferably will range from 0.01 µm to approximately 20 µm.

The amino acid compounds in accordance with the present invention can be used as UV screening agents for the anti-sun/sunscreen protection of the human skin and of the hair. They can also be employed as light photoprotective agents in those industries relating to plastics, textiles, glass (containers, optical glasses, in particular eyeglasses) and other industrial materials/substrates, such as foodstuffs.

The compound or compounds of formula (I) are advantageously formulated into the cosmetic compositions according to the invention in proportions ranging from 0.1% to 20% by weight with respect to the total weight of the composition, preferably from 0.1% to 15%.

The cosmetic compositions of the invention are useful protective compositions for the human epidermis, or for the hair, or as anti-sun/sunscreen compositions.

The anti-sun/sunscreen cosmetic compositions according to the invention can, of course, comprise one or more additional, hydrophilic or lipophilic, organic anti-sun/sunscreen screening agents which are active in the UV-A and/or UV-B regions (absorbers), other than the screening agents indicated above. These additional organic screening agents are advantageously selected, in particular, from among the cinnamic derivatives, dibenzoylmethane derivatives, salicylic derivatives, camphor derivatives, triazine derivatives, such as those disclosed in U.S. Pat. No. 4,367,390, EP-863,145, EP-517,104, EP-570,838, EP-796,851, EP-775,698, EP-878,469 and EP-933,376, benzophenone derivatives, β,β-diphenylacrylate derivatives, benzimidazole derivatives, bisbenzoazolyl derivatives, such as those disclosed in EP-A-0,669,323 and U.S. Pat. No. 2,463,264, bishydroxyphenolbenzotriazole derivatives, such as those described in U.S. Pat. Nos. 5,237,071 and 5,166,355, GB-A-2,303,549, DE-19,726,184 and EP-A-893,119, p-aminobenzoic acid derivatives, or screening hydrocarbonaceous polymers and screening silicones, such as those described, in particular, in WO-93/04665.

Exemplary sunscreens which are active in the UVA and/or UVB regions include:

p-aminobenzoic acid;
oxyethylenated (25 mol) p-aminobenzoate;
2-ethylhexyl p-dimethylaminobenzoate;
N-oxypropylenated ethyl p-aminobenzoate;
glycerol p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl 2-cyano-3,3-diphenylacrylate;
ethyl 2-cyano-3,3-diphenylacrylate;
2-phenylbenzimidazole-5-sulfonic acid and salts thereof;
3-(4'-trimethylammonio)benzylidenebornan-2-one methyl sulfate;
2-hydroxy-4-methoxybenzophenone;
2-hydroxy4-methoxybenzophenone-5-sulfonate;
2,4-dihydroxybenzophenone;
2,2',4,4'-tetrahydroxybenzophenone;
2,2'-dihydroxy-4,4'-dimethoxybenzophenone;
2-hydroxy-4-(n-octoxy)benzophenone;
2-hydroxy-4-methoxy-4'-methylbenzophenone;
α-(2-oxoborn-3-ylidene)toluene-4-sulfonic acid and soluble salts thereof;
3-(4'-sulfo)benzylidenebornan-2-one and soluble salts thereof;
3-(4'-methylbenzylidene)-d,1-camphor;
3- benzylidene-d,1-camphor;
benzene-1,4-di(3-methylidene-10-camphorsulfonic acid) and soluble salts thereof;
urocanic acid;
2,4,6-tris[p-(2'-ethylhexyl-1'-oxycarbonyl)anilino]-1,3,5-triazine;
2-[p-(tert-butylamido)anilino]-4,6-bis[p-(2'-ethylhexyl-1'-oxycarbonyl) anilino]-1,3,5-triazine;
2,4-bis[4-(2-ethylhexyloxy)-2-hydroxyphenyl]-6-(4methoxyphenyl) -1,3,5-triazine;
the polymer of N-[(2- and 4-)[(2-oxoborn-3-ylidene)-methyl]benzyl]acrylamide;
1,4-bisbenzimidazolylphenylene-3,3',5,5'-tetrasulfonic acid and soluble salts thereof;
2,2'-methylenebis[6-(2H-benzotriazol-2-yl)-4(1,1,3,3tetramethylbutyl) phenol];
the compound 2,2'-methylenebis[6-(2H-benzotriazol-2yl)-4-(methyl)phenol];
polyorganosiloxanes comprising a benzalmalonate functional group;
polyorganosiloxanes comprising a benzotriazole functional group, such as Drometrizole Trisiloxane.

The compositions according to the invention can also include agents for the artificial tanning and/or browning of the skin (self-tanning agents), such as, for example, dihydroxyacetone (DHA).

The cosmetic compositions according to the invention can also include pigments or, alternatively, nanopigments (mean size of the primary particles: generally ranging from 5 nm to 100 nm, preferably from 10 nm to 50 nm) formed of metal oxides which are coated or uncoated, such as, for example, titanium dioxide (amorphous or crystallized in the rutile and/or anatase form), iron oxide, zinc oxide, zirconium oxide or cerium oxide nanopigments or mixtures thereof which are all UV photoprotective agents well known per se. Furthermore, alumina and/or aluminum stearate are conventional coating agents. Such coated or uncoated metal oxide nanopigments are described, in particular, in EP-A-0,518,772 and EP-A-0,518,773.

The compositions of the invention can additionally comprise conventional cosmetic adjuvants and additives selected, in particular, from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, propellants, basifying or acidifying agents, polymers, colorants, dyes or any other ingredient conventionally included in cosmetics, in particular for the formulation of anti-sun/sunscreen compositions in the form of emulsions.

The fatty substances can be composed of an oil or a wax or mixtures thereof and they also comprise fatty acids, fatty alcohols and fatty acid esters. The oils are advantageously selected from among animal, vegetable, mineral or synthetic oils and, in particular, from among liquid petrolatum, liquid paraffin, volatile or non-volatile silicone oils, isoparaffins, poly-α-olefins, or fluorinated and perfluorinated oils. Similarly, the waxes are advantageously selected from among animal, fossil, vegetable, mineral or synthetic waxes, per se known to this art.

Exemplary organic solvents include the lower alcohols and polyols.

The thickeners are advantageously selected, in particular, from among the crosslinked homopolymers of acrylic acid or from among the modified or unmodified guar gums and celluloses, such as hydroxypropylated guar gum, methylhydroxyethyl-cellulose, hydroxypropylmethyl cellulose or hydroxyethylcellulose.

Too, one skilled in this art will take care to select this or these optional additional compounds and/or the amounts thereof such that the advantageous properties intrinsically associated with the amino acid derivatives in accordance with the invention are not, or are not substantially, detrimentally affected by the envisaged addition or additions.

The compositions of the invention can be formulated according to techniques well known to this art, in particular those suited for the preparation of emulsions of oil-in-water or water-in-oil type.

Such compositions can be provided, advantageously, in the form of a simple or complex emulsion (O/W, W/O, O/W/O or W/O/W), such as a cream, a milk, a gel or a cream gel, a lotion, an ointment, a powder or a solid stick and can optionally be packaged as an aerosol and provided in the form of a foam or spray.

When formulated as an emulsion, the aqueous phase thereof can comprise a nonionic vesicular dispersion prepared according to known techniques (Bangham, Standish and Watkins, *J. Mol. Biol.,* 1965, 13, 238, FR-2,315,991 and FR-2,416,008).

The cosmetic compositions of the invention can be formulated as compositions for protecting the human epidermis or the hair against ultraviolet radiation as an anti-sun/sunscreen composition or as a makeup product.

When the cosmetic compositions according to the invention are formulated for the protection of the human epidermis against UV rays or as an anti-sun/sunscreen composition, same can be provided in the form of a suspension or dispersion in solvents or fatty substances, in the form of a nonionic vesicular dispersion or in the form of an emulsion, preferably of oil-in-water type, such as a cream or a milk, in the form of an ointment, gel, cream gel, solid stick, aerosol foam or spray.

When the cosmetic compositions according to the invention are formulated for the protection of the hair, same it can be provided in the form of a shampoo, lotion, gel, emulsion or nonionic vesicular dispersion and can constitute, for example, a rinse-out composition, to be applied before or after shampooing, before or after dyeing or bleaching and before, during or after permanent waving or hair straightening, a styling or treating lotion or a styling or treating gel, a lotion or a gel for blow drying or hair setting, or a composition for permanent waving or straightening, dyeing or bleaching the hair.

When the subject compositions are suited as products for making up the eyelashes, eyebrows or skin, such as a treatment cream for the epidermis, foundation, lipstick, eyeshadow, face powder, mascara or eyeliner, same can be provided in the anhydrous or aqueous, pasty or solid form, such as oil-in-water or water-in-oil emulsions, nonionic vesicular dispersions, or suspensions.

For example, for the anti-sun/sunscreen formulations in accordance with the invention which include a vehicle of oil-in-water emulsion type, the aqueous phase (comprising in particular the hydrophilic screening agents) generally constitutes from 50% to 95% by weight, preferably from 70% to 90% by weight, with respect to the total weight of the formulation, the oily phase (comprising in particular the lipophilic screening agents) from 5% to 50% by weight, preferably from 10% to 30% by weight, with respect to the total weight of the formulation, and the (co)emulsifier(s) from 0.5% to 20% by weight, preferably from 2% to 10% by weight, also with respect to the total weight of the formulation.

The present invention also features formulating at least one compound of formula (I) into compositions well suited for the photoprotection of industrial materials and substrates which are sensitive to ultraviolet radiation, in particular to solar radiation.

Too, the present invention features formulating at least one compound of formula (I) into cosmetic compositions well suited for the photoprotection of the skin and/or hair against the damaging effects of ultraviolet radiation, in particular solar radiation.

The aforementioned photosensitive industrial materials and substrates can, in particular, be organic and/or inorganic glasses, plastics, textiles, paints, varnishes, foodstuffs, and the like.

The compounds of the invention can be applied in an effective amount onto the surface of said photosensitive industrial materials/substrates or else can be incorporated directly into the composition or body of said industrial materials/substrates.

This invention thus features a technique for the protection of a photosensitive industrial material/substrate against the harmful effects of UV radiation, in particular solar radiation, by incorporating, in said material/substrate, an effective photoprotecting amount of a compound of formula (I).

In another embodiment of the invention, the protection process entails applying, onto the face surface(s) of said photosensitive industrial material/substrate, an effective photoprotecting amount of a compound of formula (I).

In order to further illustrate the present invention and the advantages thereof, the following specific examples are given, it being understood that same are intended only as illustrative and in nowise limitative.

EXAMPLE 1

Preparation of N$^\epsilon$-cinnamoyl-L-lysine (trans-geometrical isomerism)

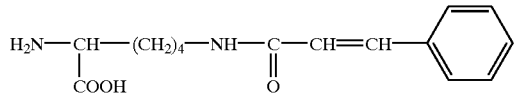

Procedure:

10 g of L-lysine monohydrochloride (54.75 mmol) were dissolved in 44 ml of 10% sodium hydroxide solution (2 equivalents) in a 250 ml three-necked flask equipped with a thermometer and a 50 ml dropping funnel. A solution of 6.8 g (0.5 equivalent) of copper sulfate pentahydrate in 40 ml of water was introduced into the reaction medium, followed by 4.6 g of sodium hydrogencarbonate and 20 ml of organic solvent (tetrahyrofuran, acetone or dimethylformamide).

A solution comprising 1 equivalent of cinnamoyl chloride in 20 ml of solvent was prepared and then introduced dropwise onto the homogeneous reaction mixture, cooled to a temperature of 5° C. After stirring overnight at ambient temperature, the reaction medium was filtered and the blue precipitate, corresponding to the final product in the copper complex form, was recovered. Said precipitate was washed with water and with acetone, and then dried in an oven under vacuum. In order to remove the copper, x mol of complex were treated at reflux for 4 hours with 3×mol of dihydrated disodium salt of ethylenediaminetetraacetic acid as a 10% solution. The treatment can be repeated several times until the decomplexed product is obtained. 8.9 g of final product were obtained, i.e., a yield of 60%.

Analyses:

Melting point (Köfler bench): >260° C. Elemental analysis ($C_{15}H_{20}N_2O_3$); molecular weight: 276.34

|  | C | H | N | O | Cu |
|---|---|---|---|---|---|
| % theory: | 65.2 | 7.3 | 10.14 | 17.37 |  |
| % found: | 65.04 | 7.36 | 9.95 | 17.35 | 698 ppm |

Number (average) particle size, measured on a Coulter Counter TA2:

1.73μm (standard deviation: 0.81 μm)

Optical rotation, determined with a Perkin-Elmer model 241 polarimeter:

[α]$_D$=+17°©=2, 6N HCl, 20° C.)

The mass and $^1$H NMR spectra were in accordance with the expected structure.

UV Absorption/Light Scattering Properties:

The UV absorption spectrum of the compound was measured as a 5% dispersion in liquid petrolatum. The total transmission and reflection of the dispersion was determined on a 60 μm film with a spectrophotometer equipped with an integrating sphere.

A solid spectrum was observed between 310 and 350 nm, which spectrum exhibited:

(a) an absorption maximum at 260 nm and a shoulder at 305 nm, (b) an optical density at 310 nm of 0.8.

EXAMPLE 2

Preparation of N-(4-methoxycinnamoyl)-L-lysine (trans-geometrical isomerism

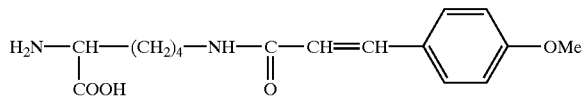

Procedure:

The preparation was carried out under the same conditions as Example 1, using 4-methoxycinnamoyl chloride as acid chloride. 6.3 g of final product were obtained, i.e., a yield of 38%.

Analyses:

Melting point (Köfler bench): >260° C. Elemental analysis ($C_{16}H_{22}N_2O_4$); molecular weight: 306.37

|  | C | H | N | O |
|---|---|---|---|---|
| % theory: | 62.73 | 7.24 | 9.14 | 20.89 |
| % found: | 62.50 | 7.22 | 9.19 | 20.88 |

Number (average) particle size, measured on a Coulter Counter TA2:

10.72 μm (standard deviation: 5.63 μm)

Optical rotation, determined with a Perkin-Elmer model 241 polarimeter:

[α]$_D$=+17.6°©=2, 6N HCl, 20° C.)

The mass and $^1$H NMR spectra were in accordance with the expected structure.

UV Absorption/Light Scattering Properties:

The UV absorption spectrum of the compound was measured as a 5% dispersion in liquid petrolatum. The total transmission and reflection of the dispersion was determined on a 60 μm film with a spectrophotometer equipped with an integrating sphere (8 trials).

A spectrum exhibiting a plateau between 310 and 250 nm was observed, which spectrum had:

(a) an absorption maximum at 300 nm and a shoulder at 320 nm, (b) an optical density at 310 nm of 0.4.

EXAMPLE 3

Preparation of N$^ε$-[4-(4,7,7-trimethyl-3-oxobicyclo [2.2.1]hept-2-ylidenemethyl) benzenesulfonyl]-L-lysine

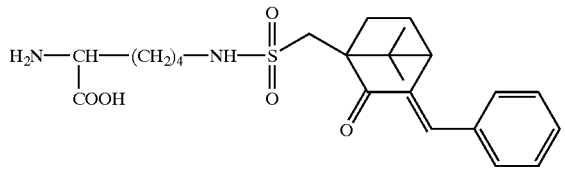

Procedure:

The preparation was carried out under the same conditions as Example 1 using 4-(4,7,7-trimethyl-3-oxobicyclo [2.2.1]hept-2-ylidenemethyl)benzenesulfonyl chloride as sulfonyl chloride. 16 g of final product were obtained, i.e., a yield of 66%.

Analyses:

Melting point (Köfler bench): 246–248° C. Elemental analysis ($C_{23}H_{32}N_2O_5S$); molecular weight: 448.58

|  | C | H | N | O | S |
|---|---|---|---|---|---|
| % theory: | 61.58 | 7.19 | 6.24 | 17.83 | 7.15 |
| % found: | 61.17 | 7.24 | 6.17 | 18.29 | 7.14 |

Number (average) particle size, measured on a Coulter Counter TA2:

1.95 μm (standard deviation: 1.05 μm)

Optical rotation, determined with a Perkin-Elmer model 241 polarimeter:

[α]$_D$=+15.5° (c=2, CH$_3$COOH, 20° C.)

The mass and $^1$H NMR spectra were in accordance with the expected structure.

UV Absorption/Light Scattering Properties:

The UV absorption spectrum of the compound was measured as a 5% dispersion in liquid petrolatum. The total transmission and reflection of the dispersion was determined on a 60 μm film with a spectrophotometer equipped with an integrating sphere (8 trials).

A spectrum exhibiting a resolved band was observed, which spectrum had:

(a) an absorption maximum at 296 nm, a first shoulder at 320 nm and a second shoulder at 282 nm;

(b) an optical density at 310 nm of 1.2.

EXAMPLE 4

The following specific composition was formulated:

| COMPOSITION (O/W emulsion) | % by weight |
|---|---|
| Mixture of glyceryl mono/distearate and of polyethylene glycol stearate (100 EO) (Arlacel 165 FL, Uniquema) | 2 |
| Stearyl alcohol (Lanette 18, Henkel) | 1 |
| Stearic acid from palm oil (Stearine TP, Stearinerie Dubois) | 2 |
| Polydimethylsiloxane (Dow Corning 200 Fluid, Dow Corning) | 1 |
| Petrolatum (White Petrolatum) | 3 |
| Liquid petrolatum (Marcol 82, Esso) | 15 |
| Polyacrylic acid (Carbopol 980, Goodrich) | 0.3 |
| $N^\epsilon$-[4-(4,7,7-Trimethyl-3-oxobicyclo[2.2.1]hept-2-ylidenemethyl)benzenesulfonyl]-L-lysine (Example 3) | 10 |
| 1,3-Butylene glycol | 10 |
| Triethanolamine | 0.4 |
| Preservatives | q.s. |
| Demineralized water | q.s. for 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic composition suited for the UV-photoprotection of human skin and/or hair, comprising an effective UV-photoprotective amount of at least one amino acid compound having the structural formula (I):

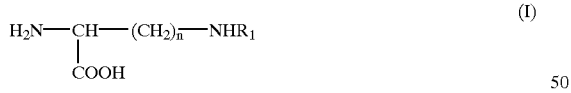

in which n is an integer ranging from 1 to 4; and $R_1$ is one of the following radicals of formula (1), (2), (3), (4), (5), (6) or (7):

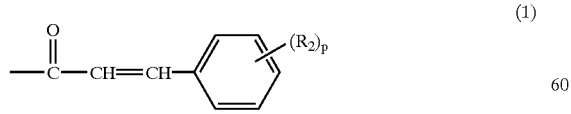

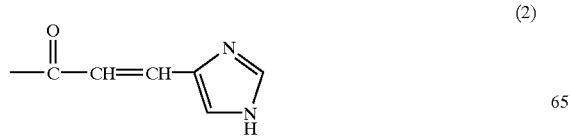

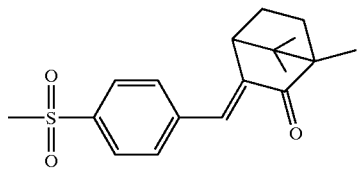

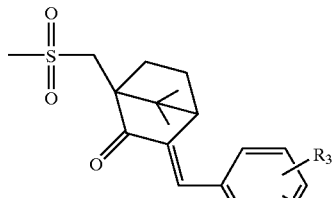

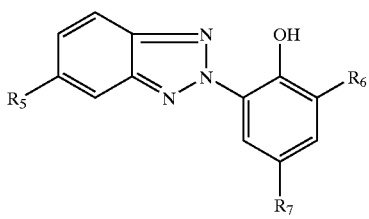

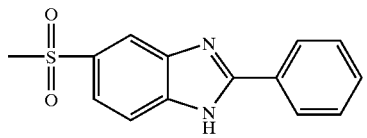

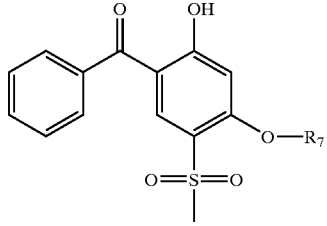

in which p is an integer ranging from 1 to 3; $R_2$ is a hydrogen atom, a $C_1$–$C_8$ alkyl radical, a $C_1$–$C_8$ O-alkyl radical, or a $C_1$–$C_8$ O-acyl radical; $R_3$ and $R_4$, which may be identical or different, are each a hydrogen or halogen atom, or $C_1$–$C_8$ alkyl or alkoxy, or a radical of the following formula (8):

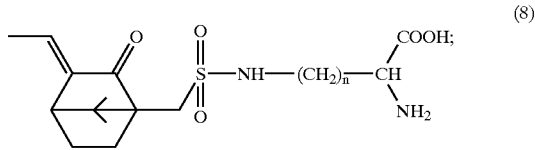

$R_5$ is a hydrogen or halogen atom, a $C_1$–$C_8$ alkyl or alkoxy radical, or a divalent radical:

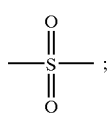

$R_6$ is a hydrogen atom, a $C_1$–$C_8$ alkyl radical, or a divalent radical:

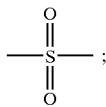

with the proviso that at least one of the two substituents $R_5$ and $R_6$ is the divalent radical:

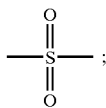

$R_7$ is a $C_1$–$C_8$ alkyl radical; or an acid or base salt thereof, formulated into a topically applicable, cosmetically acceptable vehicle, diluent or carrier therefor.

2. The photoprotective cosmetic composition as defined by claim 1, wherein formula (I), n=3 (ornithine compound) or n=4 (lysine compound).

3. The photoprotective cosmetic composition as defined by claim 2, said amino acid compound of formula (I) being $N^\epsilon$-cinnamoyl-L-lysine; $N^\epsilon$-(4-methoxycinnamoyl)-L-lysine; or $N^\epsilon$-[4-(4,7,7-trimethyl-3-oxobicyclo[2.2.1]hept-2-ylidenemethyl)benzenesulfonyl]-L-lysine.

4. The photoprotective cosmetic composition as defined by claim 1, comprising particulates of the amino acid compound of formula (I), the mean particle size of which being less than 50 µm.

5. The photoprotective cosmetic composition as defined by claim 4, said particulates having a mean particle size ranging from about 0.01 µm to about 20 µm.

6. The photoprotective cosmetic composition as defined by claim 1, comprising from 0.1% to 20% by weight of said at least one amino acid compound of formula (I).

7. The photoprotective cosmetic composition as defined by claim 1, comprising an oil-in-water emulsion.

8. The photoprotective cosmetic composition as defined by claim 1, further comprising at least one additional, hydrophilic or lipophilic, organic screening agent active in the UV-A and/or UV-B regions.

9. The photoprotective cosmetic composition as defined by claim 8, said at least one additional organic screening agent being selected from among cinnamic derivatives, dibenzoylmethane derivatives, salicylic derivatives, camphor derivatives, triazine derivatives, benzophenone derivatives, β,β-diphenylacrylate derivatives, benzimidazole derivatives, bisbenzoazolyl derivatives, bishydroxyphenolbenzotriazole derivatives, p-aminobenzoic acid derivatives, or screening hydrocarbonaceous polymers and screening silicones.

10. The photoprotective cosmetic composition as defined by claim 1, further comprising at least one additional UV-photoprotective agent selected from among coated or uncoated metal oxide pigments or nonopigments.

11. The photoprotective cosmetic composition as defined by claim 10, comprising pigments or nanopigments of titanium, zinc, iron, zirconium or cerium oxides and mixtures thereof.

12. The photoprotective cosmetic composition as defined by claim 1, further comprising at least one agent for the artificial tanning and/or browning of the skin.

13. The photoprotective cosmetic composition as defined by claim 1, further comprising at least one adjuvant or additive selected from among fatty substances, organic solvents, thickeners, softeners, antioxidants, opacifiers, stabilizers, emollients, hydroxy acids, antifoaming agents, moisturizing agents, vitamins, fragrances, preservatives, surfactants, fillers, sequestering agents, polymers, propellants, bastifying or acidifying agents, or dyes or colorants.

14. The photoprotective cosmetic composition as defined by claim 1, comprising a nonionic vesicular dispersion, a cream, a milk, a gel, a cream gel, a lotion, a suspension, an ointment, a dispersion, a paste, a powder, a solid, a shampoo, a foam or a spray.

15. The photoprotective cosmetic composition as defined by claim 1, comprising a makeup for the eyelashes, eyebrows or skin.

16. A regime/regimen for protecting human skin and/or hair against the deleterious effects of ultraviolet irradiation, comprising topically applying thereon an effective UV-photoprotecting amount of the photoprotecting cosmetic composition as defined by claim 1.

* * * * *